United States Patent
Venkatesh et al.

(10) Patent No.: US 7,632,521 B2
(45) Date of Patent: Dec. 15, 2009

(54) CONTROLLED RELEASE POTASSIUM CHLORIDE TABLETS

(75) Inventors: Gopi Venkatesh, Vandalia, OH (US); Craig Kramer, West Carrollton, OH (US)

(73) Assignee: Eurand, Inc., Vandalia, OH (US)

( * ) Notice: Subject to any disclaimer, the term of this patent is extended or adjusted under 35 U.S.C. 154(b) by 414 days.

(21) Appl. No.: 10/619,924

(22) Filed: Jul. 15, 2003

(65) Prior Publication Data
US 2005/0013860 A1  Jan. 20, 2005
US 2008/0279937 A2  Nov. 13, 2008

(51) Int. Cl.
*A61K 9/14* (2006.01)
*A61K 9/16* (2006.01)
*A61K 9/20* (2006.01)
*A61K 9/22* (2006.01)
*A61K 9/26* (2006.01)

(52) U.S. Cl. ............. 424/468; 424/464; 424/469; 424/470; 424/489; 424/490; 424/493; 424/494; 424/495

(58) Field of Classification Search ................ None
See application file for complete search history.

(56) References Cited

U.S. PATENT DOCUMENTS

| | | | |
|---|---|---|---|
| 2,887,440 A | 5/1959 | Greminger, Jr. et al. | |
| 3,155,590 A | 11/1964 | Miller et al. | |
| 3,242,051 A | 3/1966 | Hlestand et al. | |
| 3,341,416 A | 9/1967 | Anderson et al. | |
| 3,354,863 A | 11/1967 | Reynolds | |
| 3,476,588 A | 11/1969 | Pitel | |
| 3,531,418 A | 9/1970 | Fanger et al. | |
| 3,538,214 A | 11/1970 | Polli et al. | |
| 3,557,279 A | 1/1971 | Morse | |
| 3,694,372 A | 9/1972 | Anderson et al. | |
| 3,732,172 A | 5/1973 | Herbig et al. | |
| 3,748,277 A | 7/1973 | Wagner | |
| 3,860,733 A | 1/1975 | Morse et al. | |
| 3,909,444 A | 9/1975 | Anderson et al. | |
| 3,939,259 A | 2/1976 | Pescetti | |
| 3,957,523 A | 5/1976 | Ohno et al. | |
| 3,960,757 A | 6/1976 | Morishita et al. | |
| 4,010,038 A | 3/1977 | Iwasaki et al. | |
| 4,128,658 A | 12/1978 | Price et al. | |
| 4,138,475 A | 2/1979 | McAinish et al. | |
| 4,140,756 A | 2/1979 | Gallian | |
| 4,150,110 A | 4/1979 | Yoshida et al. | |
| 4,182,778 A | 1/1980 | Hall et al. | |
| 4,193,985 A | 3/1980 | Bechgaard et al. | |
| 4,259,315 A | 3/1981 | Lippmann et al. | |
| 4,302,440 A | 11/1981 | John et al. | |
| 4,316,884 A | 2/1982 | Alam et al. | |
| 4,321,253 A | 3/1982 | Beatty | |
| 4,389,330 A | 6/1983 | Tice et al. | |
| 4,389,331 A | 6/1983 | Samejima et al. | |
| 4,432,966 A | 2/1984 | Zeitun et al. | |
| 4,460,563 A | 7/1984 | Calanchi | |
| 4,462,982 A | 7/1984 | Samejima et al. | |
| 4,508,702 A | 4/1985 | Hsiao | |
| 4,519,801 A | 5/1985 | Edgren | |
| 4,524,060 A | 6/1985 | Mughal et al. | |
| 4,542,042 A | 9/1985 | Samejima et al. | |
| 4,553,973 A | 11/1985 | Edgren | |
| 4,555,399 A | 11/1985 | Hsiao | |
| 4,572,833 A | 2/1986 | Pedersen et al. | |
| 4,574,080 A | 3/1986 | Roswall et al. | |
| 4,587,118 A | 5/1986 | Hsiao | |
| 4,629,620 A | 12/1986 | Lindahl et al. | |
| 4,634,587 A | 1/1987 | Hsiao | |
| 4,666,703 A * | 5/1987 | Kopf | 424/470 |
| 4,713,248 A | 12/1987 | Kjornaes et al. | |
| 4,716,041 A | 12/1987 | Kjornaes et al. | |
| 4,748,023 A | 5/1988 | Tamas et al. | |
| 4,777,044 A * | 10/1988 | Bins | 424/718 |
| 4,800,087 A | 1/1989 | Mehta | |
| 4,820,627 A | 4/1989 | McGeehan | |
| 4,832,955 A | 5/1989 | Snipes et al. | |

(Continued)

FOREIGN PATENT DOCUMENTS

CA  2068366  11/1992

(Continued)

OTHER PUBLICATIONS

Remington: The Science and Practice of Pharmacy. vol. 2, pp. 1615-1621, 1995.*

(Continued)

*Primary Examiner*—S. Tran
(74) *Attorney, Agent, or Firm*—Cooley Godward Kronish, LLP

(57) ABSTRACT

A unit dosage form, such as a tablet for delivering potassium into the body in a controlled release fashion, comprises of a multiplicity of microencapsulated potassium chloride crystals, which are further coated with a plasticized polymer to improve compressibility of the microcapsules. The compressible microcapsules are blended with a compression aid, such as microcrystalline cellulose and a glidant, such as colloidal silicon dioxide, to form controlled release potassium chloride tablets. The tablets may optionally include other excipients such as surfactants and disintegrants. The tablets thus produced exhibit not only high crushing strength and low friability but also release potassium in humans in a desired controlled release fashion similar to commercially available potassium chloride tablets.

27 Claims, 3 Drawing Sheets

U.S. PATENT DOCUMENTS

| | | | |
|---|---|---|---|
| 4,863,743 A | 9/1989 | Hsiao et al. | |
| 4,895,836 A * | 1/1990 | Chiodini et al. | 514/26 |
| 4,898,737 A | 2/1990 | Panoz et al. | |
| 4,915,953 A | 4/1990 | Jordan et al. | |
| 4,952,402 A | 8/1990 | Sparks et al. | |
| 4,954,349 A * | 9/1990 | Sheth et al. | 424/461 |
| 4,971,791 A | 11/1990 | Tsau et al. | |
| 4,994,260 A | 2/1991 | Kallstrand et al. | |
| 5,002,774 A | 3/1991 | Agrawala et al. | |
| 5,008,117 A | 4/1991 | Calanchi et al. | |
| 5,032,406 A | 7/1991 | Dansereau et al. | |
| 5,073,374 A | 12/1991 | McCarty | |
| 5,073,377 A | 12/1991 | Alexander et al. | |
| 5,075,114 A | 12/1991 | Roche | |
| 5,082,669 A | 1/1992 | Shirai et al. | |
| 5,084,278 A | 1/1992 | Mehta | |
| 5,085,868 A | 2/1992 | Mattsson et al. | |
| 5,126,145 A | 6/1992 | Evenstad et al. | |
| 5,133,974 A | 7/1992 | Paradissis et al. | |
| 5,137,730 A | 8/1992 | Dennis et al. | |
| 5,156,850 A | 10/1992 | Wong et al. | |
| 5,178,878 A | 1/1993 | Wehling et al. | |
| 5,180,587 A | 1/1993 | Moore | |
| 5,192,552 A | 3/1993 | Fekete et al. | |
| 5,215,756 A | 6/1993 | Gole et al. | |
| 5,219,574 A | 6/1993 | Wehling et al. | |
| 5,223,264 A | 6/1993 | Wehling et al. | |
| 5,229,134 A | 7/1993 | Mention et al. | |
| 5,238,688 A | 8/1993 | Beuving et al. | |
| 5,252,337 A | 10/1993 | Powell | |
| 5,397,574 A | 3/1995 | Chen | |
| 5,409,711 A | 4/1995 | Mapelli et al. | |
| 5,422,122 A | 6/1995 | Powell | |
| 5,464,632 A | 11/1995 | Cousin et al. | |
| 5,472,712 A * | 12/1995 | Oshlack et al. | 424/480 |
| 5,505,962 A | 4/1996 | Sparks | |
| 5,567,441 A | 10/1996 | Chen | |
| 5,578,316 A | 11/1996 | Bhardwaj et al. | |
| 5,622,723 A | 4/1997 | Bettman et al. | |
| 5,639,475 A | 6/1997 | Bettman et al. | |
| 5,651,984 A | 7/1997 | Powell | |
| 5,653,993 A | 8/1997 | Ghanta et al. | |
| 5,709,886 A | 1/1998 | Bettman et al. | |
| 5,807,579 A * | 9/1998 | Vilkov et al. | 424/469 |
| 5,814,332 A | 9/1998 | Ghanta et al. | |
| 5,840,329 A | 11/1998 | Bai | |
| 5,879,706 A | 3/1999 | Carter et al. | |
| 6,139,865 A | 10/2000 | Friend et al. | |
| 6,210,716 B1 | 4/2001 | Chen et al. | |
| 6,316,031 B1 | 11/2001 | Oshlack et al. | |
| 6,451,345 B1 | 9/2002 | Percel et al. | |
| 2006/0222699 A1* | 10/2006 | Gilinski | 424/451 |
| 2008/0207673 A1* | 8/2008 | Xilinas | 514/292 |

FOREIGN PATENT DOCUMENTS

| | | |
|---|---|---|
| CA | 2068402 | 12/1992 |
| EP | 0076515 | 4/1983 |
| EP | 0317274 | 5/1989 |
| EP | 0411952 | 2/1991 |
| GB | 978265 | 12/1964 |
| GB | 1016839 | 1/1966 |
| GB | 1371840 | 10/1974 |
| WO | WO 92/19209 | 11/1992 |
| WO | WO 98/14179 | 4/1998 |
| WO | WO 9814179 A1 * | 4/1998 |
| WO | WO 0143725 A1 * | 6/2001 |

OTHER PUBLICATIONS

U.S. Appl. No. 09/465,085, filed Dec. 1999, Venktesh et al.

Deasy, P.B et al., "Effect of ethylcellulose grade and sealant treatments on the production and in vitro release of microencapsulated sodium salicylate," *J. Pharm. Pharmacol*, 32: 15-20. (1980).

Friend, D.R., "Polyacrylate resin microcapsules for taste masking of antibiotics," *J. Miroencapsulation*, vol. 9, No. 4, pp. 469-480 (1992).

Ueda, M. "Recent Pharmaceutical Techniques and Future Scope for Taste Masking of Granules," *The Annual Proceedings of Gifu Pharmaceutical University*, vol. 44, p. 18-31 (Jun. 1995).

Kristl, A. et al., "Preparation and Evaluation of Ethylcellulose Microcapsules with Bacampicillin," *Drug Development and Industrial Pharmacy*, 17(8), pp. 1109-1130 (1991).

Chemtob, C. et al., "Microencapsulation by ethylcellulose phase separation: microcapsule characteristics," *International Journal of Pharmaceutics*, 29, pp. 1-7 (1986).

Sveinsson, S.J. et al., "The effect of tableting on the release characteristics of naproxen and ibuprofen microcapsules," *International Journal of Pharmaceutics*, 92, pp. 29-34 (1993).

Versic, R.J., "Coacervation for Flavor Encapusulation," *ACS Symposium Series 37—Flavor Encapsulation*, Chapter 14, pp. 126-131 (1987).

Roy, G.M., "Taste Masking in Oral Pharmaceuticals," *Pharmaceutical Technology* (Apr. 1994).

Deasy, P.W., "Coacervation—Phase Separation Procedures Using Nonaqueous Vehicles," *Microencapsulation and Related Drug Processes*, pp. 97-117 (1984).

Ozer, A.Y. et al., "Studies on the masking of unpleasant taste of beclamide: microencapsulation and tabletting," *J. Microencapsulation*, vol. 7, pp. 327-339 (1990).

Gupta R.G. et al., "Micro-Encapsulation Studies of Chloroquine Phosphate for its Taste Abatement," *The Eastern Pharmacist*, pp. 133-137 (Jul. 1983).

Chukwu, A. et al., "Some properties of chloroquine phosphate and quinine hydrochloride microcapsules," *S.T.P. Pharma. Sciences*, vol. 1(2), pp. 117-120 (1991).

Ueda, M., "Recent Pharmaceutical Techniques and Outlook for Masking the Bitter Taste of Granules," *Gifu Yakuka Daigaku Kiyo*, 44, pp. 18-31 (1995).

Samuelov, Y. et al., "Sustained Release of Drugs from Ehtylcellulose-Polyethylene Glycol Films and Kinetics of Drug Release," *Journal of Pharmaceutical Sciences*, vol. 68, No. 3, pp. 325-329 (Mar. 1979).

Donbrow, M. et al., "Enhancement of permeability of ethyl cellulose films for drug penetration," *Journal of Phramacy and Pharmacology*, vol. 27, No. 9, pp. 633-646 (Sep. 1975).

Donbrow, M. et al., "Zero order drug delivery from double-layered porous films: release rate profiles from ethyl cellulose, hydroxypropyl cellulose and polyethylene glycol mixtures," *Journal of Pharmacy and Pharmacology*, vol. 32, No. 7, pp. 463-470 (1980).

Rowe, R. C., "The effect of the molecular weight of ethyl cellulose on the drug release properties of mixed films of ethyl cellulose and hydroxypropyl methylcellulose," *International Journal of Pharmaceutics*, vol. 29, No. 1, pp. 37-41 (Mar. 1986).

Donbrow, M. et al., "Permeability of films of ethyl cellulose and PEG to caffeine," *Journal of Pharmacy and Pharmacology*, vol. 26, pp. 148-150 (Feb. 1974).

Rowe, R.C., "Some Fundamental Properties of Polymeric Materials and Their Application in Film Coating Formulations—A Review," *Int. J. Pharm. Tech & Prod. Mfr.*, 3(1), pp. 3-8 (1982).

* cited by examiner ent that the described process or method of manufacturing of controlled release of potassium chloride tablets fails to meet all of the industrial applicability criteria, namely, product quality, suitability for packaging in HDPE bottles and blisters for storage, transportation, commercial distribution, and use.
CONTROLLED RELEASE POTASSIUM CHLORIDE TABLETS

TECHNICAL FIELD

A major requirement in patients treated simultaneously with diuretics and carbenoxolone is to release potassium in the body in a controlled release fashion so as to maintain the extracellular and intracellular concentrations within relatively narrow limits in order to avoid achieving life-threatening toxicity. U.S. Pat. No. 4,863,743 to Hsiao and Chou of Key Pharmaceuticals (hereafter referred to as Hsiao) discloses once a day controlled release pharmaceutical dosage forms as Potassium Chloride Extended Release Tablets, 10 and 20 mEq, comprising dissolution rate controlling membrane coated potassium chloride crystals. These tablets with acceptable hardness and friability rapidly disperse into granules on contact with water or body fluids, and the granules thus produced provide an extended release of potassium for treating potassium deficiency in humans. The present invention relates to a unit dosage form, such as a 20 mEq potassium chloride tablet for delivering potassium into the human body in a controlled release fashion, similar to that of tablets prepared in accordance with the Hsiao disclosure, and suitable for all three modes of oral administration listed in Physicians' Desk Reference for K-Dur® (page 3047 of PDR Edition 57, 2003), thus meeting all industrial applicability criteria, namely, product quality, transportation, commercial distribution, and use.

BACKGROUND OF THE INVENTION

U.S. Pat. No. 4,748,023 discloses a process for the preparation of sustained release solid pharmaceutical compositions comprising active ingredient crystals coated with a single layer of ethylcellulose, while U.S. Pat. Nos. 4,259,315, 4,572,833, and 4,832,955 disclose the preparation of sustained release solid pharmaceutical compositions comprising a potassium chloride core coated with a water insoluble ethylcellulose layer containing a hydrophobic material, a high HLB surfactant, and an amphiphile, respectively. U.S. Pat. No. 4,863,743 to Hsiao and Chou of Key Pharmaceuticals teaches a controlled release pharmaceutical dosage form comprising a dissolution rate controlling membrane on potassium chloride crystals. The dissolution rate controlling membrane includes a high viscosity water insoluble ethylcellulose in combination with a water-soluble hydroxypropylcellulose or polyethylene glycol applied from a fluid bed coater. The coated granules are blended with highly compressible microcrystalline cellulose, a disintegrant, and a lubricant (for example, magnesium stearate) and compressed into 10 or 20 mEq tablets. The resulting tablets are of acceptable hardness and friability (for example, 20 mEq tablets weighing about 2 g, exhibit a hardness of not less than 14 kP and a friability of not more than 0.3). The controlled release tablets thus produced rapidly disperse into granules upon exposure to water or body fluids, and these granules provide an extended release of potassium, i.e., releasing not more than 40% in one hour, from about 60% to about 75% in 4 hours, and not less than 80% in 8 hours when tested by USP Apparatus 2 (Paddles @ 50 rpm) in purified water. Thus, these tablets can be transported in normal storage drums for commercial distribution to pharmacies and hospitals.

Powell, in U.S. Pat. Nos. 5,422,122 and 5,651,984, teaches the preparation of controlled release 10 and 20 mEq potassium chloride tablets by first forming KCl microcapsules by coacervation in a cyclohexane solution of high viscosity water insoluble ethylcellulose and over-coating the microcapsules with at least one hydrophilic polymer to impart compressibility properties to otherwise poorly compressible microcapsules. The coated microcapsules are blended with highly compressible microcrystalline cellulose and a disintegrant to be compressed into tablets. Tablets produced from microcapsules coated with hydroxypropylcellulose exhibit the desired drug release characteristics (high hardness and low friability, providing controlled release profiles). However, compression of a mixture wherein the microcapsules are coated with hydroxypropyl methylcellulose (HPMC) or polyvinylpyrrolidone (PVP) and blended with microcrystalline cellulose, crosslinked PVP (disintegrant) and magnesium chloride failed to produce tablets of acceptable hardness and friability. Moreover, controlled release tablets comprising potassium chloride microcapsules coated with a plasticized hydroxypropyl methylcellulose or polyvinylpyrrolidone, highly compressible microcrystalline cellulose, and a disintegrant exhibited drug release profiles faster than the reference tablets (Hsiao tablets or K-Dur 20). By contrast, the tablets containing none of the widely used disintegrants exhibited in vitro drug release profiles similar to that of the Hsiao tablets and hence, proved to be bioequivalent to the Hsiao tablets. However, these tablets failed to meet the 'industrial use' test criterion because they failed to rapidly disperse into granules on contact with water. It is thus apparent that the described process or method of manufacturing of controlled release of potassium chloride tablets fails to meet all of the industrial applicability criteria, namely, product quality, suitability for packaging in HDPE bottles and blisters for storage, transportation, commercial distribution, and use.

SUMMARY OF THE INVENTION

The present invention is related to several improvements made to the process and method for preparing controlled release potassium chloride tablets disclosed by Powell in commonly assigned U.S. Pat. Nos. 5,422,122 and 5,651,984. More particularly, the present invention relates to a controlled release potassium chloride tablet prepared from a multiplicity of ethylcellulose microencapsulated potassium chloride crystals, which are further coated with a plasticized polymeric coating to impart better compressibility properties to the coated microcapsules. In accordance with certain embodiments, the coated microcapsules are blended with microcrystalline cellulose, a glidant, such as colloidal silicon dioxide, and optionally a disintegrant, such as crosslinked polyvinylpyrrolidone (Crospovidone), or a disintegrant in combination with a surfactant such as sodium lauryl sulfate, and compressed into 20 mEq oral controlled release potassium chloride tablets. The resulting tablets exhibit drug release profiles similar to that of the Hsiao tablets while providing acceptable hardness and friability. In accordance with certain embodiments, the tablets rapidly disperse into granules on contact with water or body fluids. Thus, the tablets manufactured in accordance with the present invention are suitable not only for transportation in normal storage drums for commercial distribution, but also for use in treating potassium deficiency in humans.

In accordance with one aspect of the present invention a process for preparing a controlled release tablet of potassium chloride is described. The process includes microencapsulating potassium chloride crystals with an inner membrane of ethylcellulose by coacervation or phase separation to form potassium chloride microcapsules, coating the potassium chloride microcapsules with an outer membrane comprising a plasticized polymer to form compressible coated microcapsules, preparing a compressible blend comprising the compressible coated microcapsules, microcrystalline cellulose (compression aid), and colloidal silicon dioxide and compressing the compressible blend into tablets. Tablets produced in accordance with this aspect of the invention exhibit tablet hardness of at least about 14 kP, friability of not more than about 0.3% and a dissolution profile substantially corresponding to the following pattern when tested by USP Apparatus 2 (Paddles @ 50 rpm) in purified water:

after 2 hours, about 30% to about 50% of the total potassium chloride is released;

after 4 hours, about 60% to about 75% of the total potassium chloride is released; and after 8 hours, not less than 80% of the total potassium chloride is released.

One embodiment of the present invention relates to a dosage form wherein a plasticized ethylcellulose is used to coat potassium chloride microcapsules comprising potassium chloride crystals having an unplasticized membrane of water-insoluble ethylcellulose around them, deposited by coacervation in cyclohexane, which allows compression into 10 or 20 mEq oral controlled release potassium chloride tablets of acceptable hardness and friability for transportation in normal storage drums for commercial distribution. Such tablets not only rapidly disperse into granules on contact with water or body fluids, but also exhibit drug release profiles similar to that of the Hsiao tablets. Consequently, these tablets are suitable for generic substitution of K-Dur 20, Potassium Chloride Extended Release Tablets, 20 mEq, USP, based on the invention disclosure of Hsiao, at pharmacies and hospitals for treating potassium deficiency in humans.

In accordance with another embodiment of the present invention the dosage form includes a glidant, which is normally used to improve the flow of poorly flowing formulations, for tableting instead of a widely used lubricant, such as magnesium stearate.

In accordance with a more particular aspect of the present invention a glidant is used at a negligible level (not more than 0.3% w/w) to provide strong tablets with exceptionally low friability (hardness range of 14-30 kP with friability range of 0.01 to 0.3% for 20 mEq tablets weighing approximately 2 g) wherein the resulting tablets not only rapidly disperse upon exposure to water or body fluids, but also provide a release profile similar to that of the Hsiao tablets.

In accordance with another embodiment, a dosage form comprising a glidant in combination with a disintegrant is described wherein the resulting tablets exhibit acceptable tableting and drug release properties (for example, an acceptable hardness of 14-30 kP and a friability range of 0.01 to 0.3% for 20 mEq tablets weighing approximately weighing ~2 g). The tablets thus produced not only rapidly disperse upon exposure to water or body fluids, but also provide controlled release profiles similar to that of the Hsiao tablets.

The present invention also relates to a method of treating or relieving potassium deficiency in humans without adverse side effects, comprising administering to a patient in need of treatment controlled release potassium chloride tablets for oral administration. The tablets comprise microencapsulated potassium chloride coated with a plasticized polymer, preferably ethylcellulose, which forms compressible microcapsules. The tablets further comprise highly compressible microcrystalline cellulose, colloidal silicon dioxide and optionally sodium lauryl and/or a disintegrant. 10 and 20 mEq potassium chloride tablets prepared in accordance with this aspect of the invention exhibit acceptable hardness and friability. Tablets containing a dispersant rapidly disperse into granules upon contact with water or body fluids and exhibit an extended release profile similar to that of the Hsiao tablets.

In accordance with certain embodiments of the present invention, potassium chloride tablets with significantly improved tableting properties are provided (e.g., tablets with a hardness of at least 14 kP, and more particularly about 15-30 kP and with a friability range of about 0.01 to 0.3%). The tablets in accordance with particular aspects of the present invention release not more than 40% of the dose in 1 hour, from about 60% to about 75% in 4 hours, and not less than 80% in 8 hours.

BRIEF DESCRIPTION OF THE DRAWINGS

The invention will be described in further detail with reference to the accompanying Figures wherein.

DETAILED DESCRIPTION OF THE INVENTION

Figure 1:
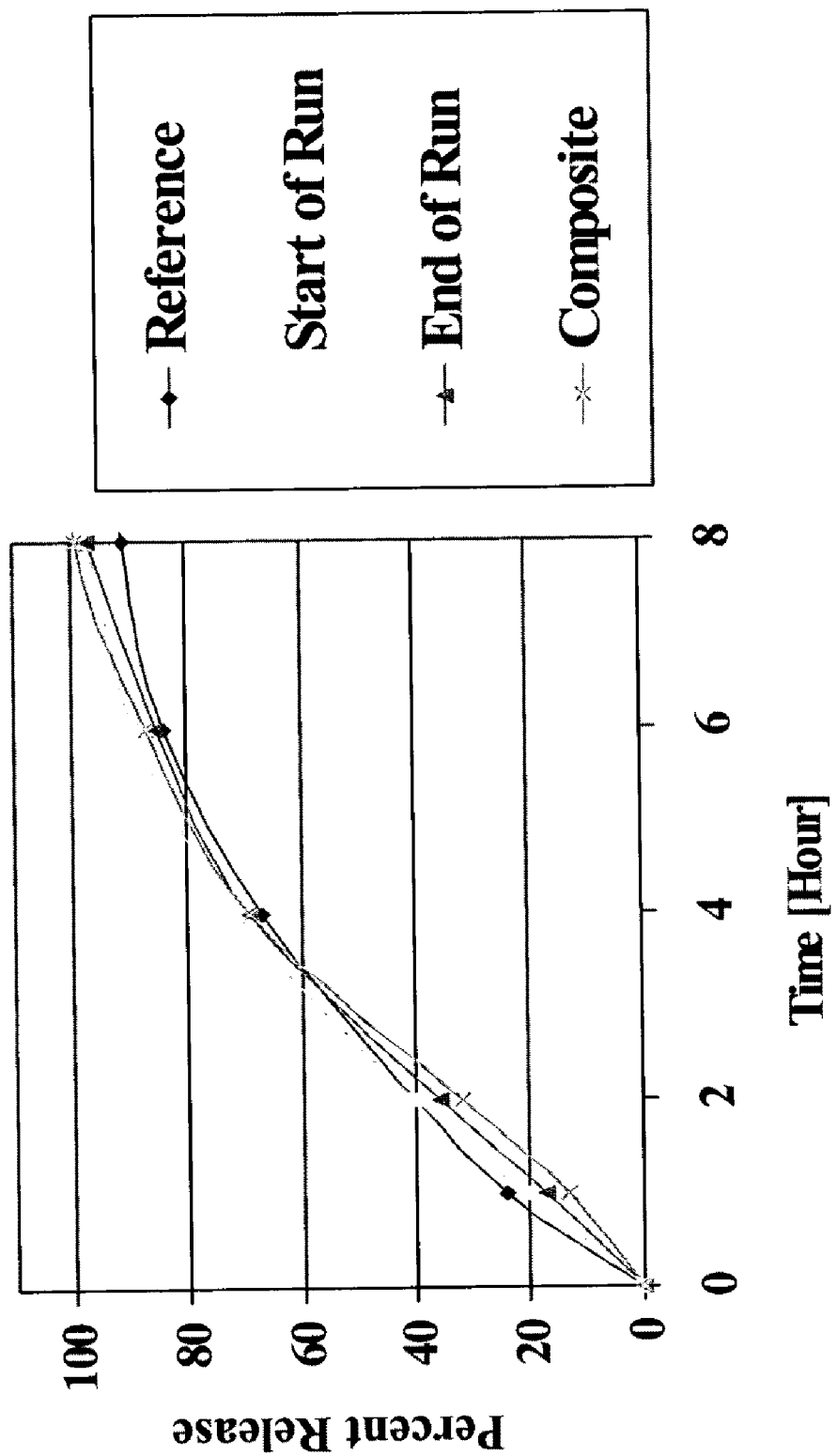
FIG. 1 shows in vitro drug release profiles for 20 mEq controlled release potassium chloride tablets of Example 10, which do not rapidly disperse into granules on contact with water or body fluids versus reference standard (K-Dur 20 or Hsiao tablets) of equal strength when dissolution tested in 900 mL of purified water at 37° C. using USP Apparatus 2 (paddles@ 50 rpm).

All documents cited are, in relevant part, incorporated herein by reference; the citation of any document is not to be construed as an admission that it is prior art with respect to the present invention.

The present invention relates to controlled release potassium chloride tablets and to processes for producing the same. The controlled release tablets provide treatment for potassium deficiency in humans while minimizing adverse side effects. The tablets of the present invention are characterized by a total tablet weight of about 2 g with acceptable hardness (not less than 14 kP) and friability (not more than 0.3%).

In accordance with the present invention, a plurality of potassium chloride crystals, typically from about 20 mesh to about 70 mesh, more particularly from about 30 mesh to about 50 mesh, are coated with two distinct layers. The first layer applied to the crystals comprises ethylcellulose. Utilization of a high viscosity ethylcellulose such as one with a viscosity of from about 90 to about 110 cps, e.g., Ethocel 100 (Dow Chemical Corp.) allows the crystals to retain their diffusion controlling characteristics even after compression into a tablet form. The ethylcellulose may be applied by any suitable technique known in the art, but is preferably applied by coacervation using polyethylene as a phase separator as described in U.S. Pat. No. 5,422,122. If coacervation is used, trace amounts of the phase separator may be present in the first layer, preferably in an amount less than about one percent by weight of the ethylcellulose coated crystals.

The ethylcellulose layer is preferably applied to the KCl crystals in an amount of about 8 to about 20 percent, more specifically from about 10 to about 17 percent, of the total weight of the potassium chloride microcapsules. This first layer controls the release of the potassium chloride over time, total release time being proportionally dependent upon the thickness of the ethylcellulose membrane. After application of the ethylcellulose, a drying step should preferably be carried out so that the residual cyclohexane level is less than 1000 parts per million. The resultant ethylcellulose encapsulated potassium chloride microcapsules are preferably of such a size that less than 5% are greater than 20 mesh.

A second, discrete layer of a plasticized compressible polymer coating, is applied as an outer membrane over the inner membrane of ethylcellulose. Pharmaceutically acceptable polymers suitable for use in the compressible coating include ethylcellulose available as an aqueous dispersion, polyvinylpyrrolidone (PVP), and hydroxypropyl methylcellulose (HPMC). This outer coating membrane may comprise from about 0.5 to about 5% based on the weight of the compressible coated microcapsules.

No plasticizer is required for the inner dissolution rate controlling membrane of the compressible coated microcapsules while the water-insoluble polymer or water-soluble polymer forming the outer membrane requires a plasticizer to impart proper compressibility properties on the ethylcellulose coated microcapsules. Representative examples of plasticizers that may be used to plasticize the outer membrane include dibutyl sebacate, diethyl phthalate, triacetin, triethyl citrate, polyethylene glycols of different molecular weights ranging from about 200 to 8,000 (e.g., a blend of PEG 400 and PEG 4000) and mixtures thereof. The plasticizer may comprise about 2 to 40 wt. % and more typically about 3 to 30 wt. % based on the weight of the plasticized polymer. The amount may vary with the type of plasticizer and the nature of the polymer. For example, for a plasticized polymer comprising HPMC and PEG400, the ratio may typically vary from about 90/10 to 97/3. For a plasticized polymer comprising PVP and DBS or triethyl citrate, the typical ratio of polymer to plasticizer can range from about 94/6 to about 97/3.

The ethylcellulose used in the outer membrane is typically applied from an aqueous dispersion of ethylcellulose. The aqueous dispersion preferably includes an effective amount of plasticizer. Commercially available ethylcellulose dispersions suitable for use in forming the outer membrane include Aquacoat® and Surelease® Aquacoat® requires the addition of a separate plasticizer, while Surelease® is supplied with a plasticizer.

The plasticized polymer is applied by conventional techniques, such as from an aqueous solution using a fluidized bed coater, to the preformed layer of ethylcellulose. The plasticized polymer coating layer inclusive of the plasticizer is applied in an amount of about 0.5 to 5% w/w (in accordance with certain embodiments, about 1 to 3% w/w and more specifically about 2% w/w) of the weight of the compressible coated microcapsules.

The plasticized polymer does not significantly diffuse into the ethylcellulose, but rather forms a distinct second layer. The first membrane of ethylcellulose coacervated in the absence of any plasticizer can be easily distinguishable from the plasticized polymeric membrane by microscopic/spectroscopic techniques. As the outer membrane layer is soluble to gastric fluids, the plasticized polymer coating dissolves following ingestion of the resultant tablet. For all practical purposes, it does not contribute to the controlled release of potassium chloride. Rather, the plasticized polymer coating is present primarily to impart compressibility to the ethylcellulose coated potassium chloride microcapsules so that a high dosage rate tablet having the necessary hardness and friability properties can be formed with a minimal amount of conventional excipients and low compaction pressures to allow minimal disruption of the rate controlling ethylcellulose membrane. In addition, this formulation allows the microencapsulated potassium chloride to be dispersed essentially intact over a wide area, reducing the risk of gastric irritation.

After the plasticized polymer coating layer is applied, the now twice coated crystals are subjected to a final drying step. The resultant coated potassium chloride microcapsules are preferably of such a size that less than 15%, are greater than 20 mesh. The coated crystals may then be formed into tablets by compression using conventional techniques. Preferably a minimal amount of excipients, no more than about 20%, preferably no more than about 15%, by weight based on the weight of the final dosage tablet, is added to the coated crystals prior to compression. The term "excipients," as used herein, refers to any additional pharmaceutically acceptable ingredients which may be used in a tablet. These excipients include, but are not limited to, ingredients such as diluents, binders, disintegrants, and wetting agents. However, these tablets in certain embodiments do not comprise any lubricant, either internally (blended intergranularly) or externally (sprayed on to the punch and die surfaces during tableting) including, but not limited to, stearates (e.g., magnesium, calcium, and sodium), stearic acid, Sterotex®, talc, waxes, and Stearowet®.

Binders include, but are not limited to, low viscosity hydroxypropyl-cellulose (Klucel® LF), polyvinylpyrrolidone (PVP), and low viscosity hydroxypropylmethylcellulose (HPMC with an average viscosity of about 3 to 15 cps). Disintegrants include, but are not limited to, cornstarch, sodium starch glycolate, Croscarmellose sodium, and Crospovidone® (cross linked polyvinyl pyrrolidone). Diluents/compression aids include, but are not limited to Avicel® or Ceolus® (microcrystalline cellulose), lactose, mannitol, Emcompress® (dibasic calcium phosphate dihydrate), and tricalcium phosphate. Surfactants (wetting agents) include, but are not limited to, sodium lauryl sulfate.

In a particular embodiment of the invention, compressible coated microcapsules comprising ethylcellulose KCl microcapsules coated with a plasticized polymer coating solution are blended with a colloidal silicon dioxide, a compression aid, preferably microcrystalline cellulose, and optionally a disintegrant and/or a surfactant to form a compressible blend. The compressible blend is compressed into capsule shaped tablets. In accordance with certain embodiments, a surfactant, such as sodium lauryl sulfate, at a level of about 0.1 to about 1.0% w/w, in combination with a disintegrant, such as Crospovidone at a level of about 0.5 to about 3% w/w, is optionally blended with the compressible blend. In the course of these investigations, it was discovered that a compressible blend comprising from about 0.1 to about 0.3%, more particularly about 0.2% colloidal silicon dioxide and not more than about 15%, more specifically not more than about 12%, and in certain embodiments not more than 10% by weight of a compression aid, preferably microcrystalline cellulose, produced strong tablets with low friability. It was also discovered that microcapsules fluid bed coated with the plasticized polymeric systems described herein could be compressed into strong tablets with low friability without a lubricant (e.g., magnesium stearate). A disintegrant normally results in a rapid disintegration of the tablet into constituent granules.

The disintegrant has been observed to speed up the drug release from the granules in certain embodiments. However, if a surfactant (sodium lauryl sulfate) is used in combination with the disintegrant, the detrimental effect of the disintegrant in terms of speeding-up of the drug release from the granules is surprisingly minimized.

The final tablets will contain a pharmaceutically acceptable amount of potassium chloride. Acceptable daily dosages may be found in The Physicians' Desk Reference, 45th ed. (1991), e.g., 20-200 mEq/day thereof, preferably from about 8 mEq to about 20 mEq. The pharmaceutically elegant 20 mEq Microcaps KCl tablets prepared in accordance with the present invention will exhibit sustained release properties (releasing not more than 40% in one hr and not less than 80% over 8 hrs when tested in USP Apparatus 2 (Paddles @ 50 rpm) in purified water, thereby providing treatments for potassium deficiency in humans with minimal adverse side effects.

In accordance with certain embodiments, the present potassium chloride tablets are substantially lubricant-free. The term "lubricant" as used herein refers to internal lubricants which are present as a component of the formulation and external lubricant applied to the material contacting punch and die surfaces to facilitate compression and ejection of the tablet from the die. As used herein, the term "substantially lubricant-free" means that conventionally used lubricants are not present in the compositions or on the die surfaces in amounts typically used to provide lubrication. Thus, it should be appreciated that reference to "substantially lubricant-free" in accordance with particular embodiments of the present invention does not exclude the presence of small amounts of lubricants as impurities. Thus, "substantially lubricant-free" should be understood as meaning free of added lubricants, and containing less than 0.5%, preferably essentially 0%, of conventional lubricants.

Tablet hardness is a physical strength measurement of the tablet. Hardness measurement provides an indication of the resistance of the tablet to chipping, abrasion, or breakage under conditions of storage, transportation and handling. Hardness is expressed as kP, Newtons, kg, or Strong Cobbs and typically measured using one of the many commonly available tablet hardness testers. Hardness in accordance with the present invention is determined using a Schleuniger Pharmatron Tablet Hardness Tester following procedures in the operation manual.

Tablet friability is a physical strength measurement of the tablet and is defined as the ability of the compressed tablet to resist abrasion and attrition. It is typically measured by turning tablets in a rotating vessel and determining weight loss. The loss of weight is measured after a fixed number of revolutions of a drum rotating in a controlled rate. Friability is determined with the present invention is determined using a Erweka Friability tester following the procedures in United States Pharmacopoeia, Volume 26, page 2439.

The following non-limiting examples illustrate the tablet dosage forms manufactured in accordance with the invention, which exhibit acceptable tableting properties (mean high hardness in the range of 14-25 kP and low friability (<0.2%)). The 20 mEq tablets comprising no disintegrant remain intact, i.e., do not disperse upon contact with water or body fluids. Still, these tablets exhibit in vitro drug release profiles similar to that of and bioequivalency to the marketed product based on the disclosure of Hsiao and Chou in U.S. Pat. No. 4,863,734. In contrast, the 20 mEq tablets comprising compressible Microcaps KCl coated with plasticized ethylcellulose and a disintegrant, or tablets comprising compressible Microcaps KCl coated with plasticized PVP or HPMC and a combination of a disintegrant and a surfactant, rapidly disperse upon contact with water and exhibit in vitro drug release profiles similar to that of the marketed product based on the disclosure of Hsiao and Chou in U.S. Pat. No. 4,863,734.

Comparative Examples 1 to 3

Example 1

Potassium chloride microcapsules were coated with an aqueous solution of low viscosity hydroxypropyl methylcellulose (HPMC, Methocel E-5 from Dow Chemical Company) and triethyl citrate at a ratio of 90/10 in a laboratory fluid bed coater for a weight of 2% w/w (batch size: 1 kg). A compression blend was prepared by blending 450 g (88%) of the compressible coated microcapsules, 48.6 g (9.5%) of microcrystalline cellulose known by the trade name as Ceolus, 10.2 g (2.0%) of Crospovidone, and 2.6 g (0.5%) of magnesium stearate and compressed into 20 mEq tablets on an R&D rotary tablet press. The tablets thus obtained exhibited extremely poor hardness (1-2 kP).

Example 2

Another batch of potassium chloride microcapsules was coated with 2% w/w of HPMC and triethyl citrate at a ratio of 80/20 as stated in Example 1. The compressible coated microcapsules (88%) were blended with Ceolus (9.5%) and Crospovidone (2%) and magnesium stearate (0.5%) and compressed into 20 mEq tablets. Poor results were obtained as in Example 1 (see Table 1).

Example 3

This batch of compressible microcapsules was obtained by coating with HPMC and polyethylene glycol (PEG 400) at a ratio of 70/30 to achieve 1% weight gain. The compressible coated microcapsules were blended with Ceolus, Crospovidone, and magnesium stearate and compressed into 20 mEq tablets. Once again extremely poor results were obtained as in Examples 1 and 2 (see Table 1).

TABLE 1

|  | Comparative Example 1 | Comparative Example 2 | Comparative Example 3 |
|---|---|---|---|
|  | Compressible Coating | | |
| Polymer | Compressible coating with HPMC | | |
| Plasticizer | Triacetin | Triacetin | PEG 400 |
| Ratio | 90/10 | 80/20 | 70/30 |
| Weight Gain | 4% w/w | 4% w/w | 1% w/w |
| Ingredients | Composition of Compressible Blend | | |
| Coated Microcapsules | 450 g | 450 g | 880 g |
| Microcrystalline cellulose | 48.6 g | 48.6 g | 100 g |
| Crosslinked povidone | 10.2 g | 10.2 g | 10 g |
| Magnesium stearate | 2.6 g | 2.6 g | 5 g |
| Sodium lauryl sulfate | 0 | 0 | 0 |
|  | 1-2 kP | 1-2 kP | 1 kP |
| Friability | Tablets disintegrated/broke under finger pressure. No friability could be tested. | | |

Comparative Examples 4 to 6

Potassium chloride microcapsules in Examples 4-6 were coated with an aqueous solution of polyvinylpyrrolidone (PVP) and dibutyl sebacate at a ratio of 97/3 in an R&D or production fluid bed coater for a weight gain of 2% w/w. While the batch size in the R&D coater was about 10 kg, the production equipment was used to coat about 700 kg of microcapsules. The tablets of examples 4 to 6 thus obtained exhibited acceptable hardness (15 kP or higher). In general, the friability values were poor, especially when scored punches were used for tableting. These tablets failed to disperse rapidly on contact with water, though the drug release profiles were similar to that of the tablets of Hsiao. From the comparative examples provided above, it is apparent that the process or the method of manufacturing of controlled release of potassium chloride tablets fails to meet the industrial applicability criteria, namely, product quality, transportation, commercial distribution, and use.

TABLE 2

|  | Comparative Example 4 | Comparative Example 5 | Comparative Example 6 |
|---|---|---|---|
|  | Compressible Coating | | |
| Glatt Coating | R&D | R&D | Production |
|  | Compressible coating with PVP with Dibutyl sebacate as the plasticizer at a ratio of 97/03 at 2% Weight gain | | |
|  | Composition of Compression Blend | | |
|  | Compressible coated Microcapsules at 90% and Microcrystalline cellulose (Ceolus) at 10% were compressed on an R&D rotary tablet press | | |
| Tooling | Scored | Scored | Unscored |
| Tablet hardness | 15.6 kP | 19.6 kP | 19.4 kP |
| Friability | 1.5% | 1.6% | 0.9% |

Comparative Examples 7-9

Example 7

A batch of compressible coated (1.5% coating of 70/30 PVP/PEG 400) microcapsules (88.5%) was compressed into 20 mEq tablets with Ceolus (10%), Crospovidone (1%), and sodium lauryl sulfate (0.5%), a surfactant which is normally used as a wetting agent. These tablets containing no lubricant exhibited good hardness but high friability.

Example 8

Potassium chloride microcapsules were coated with an aqueous solution of polyvinylpyrrolidone (PVP) and triethyl citrate at a ratio of 94/6 in a laboratory fluid bed coater for a weight gain of 2% w/w. A compression blend was prepared by blending 442.5 g of the compressible coated microcapsules, 50 g of microcrystalline cellulose known by the trade name as Ceolus, 5 g of Crospovidone, and 2.5 g of sodium lauryl sulfate and compressed into 20 mEq tablets on a rotary tablet press. The tablets thus obtained exhibited moderate hardness (10.2 kP) although the friability was poor.

Example 9

Potassium chloride microcapsules were coated with an aqueous solution of polyvinylpyrrolidone (PVP) and dibutyl sebacate at a ratio of 97/3 in a production fluid bed coater for a weight gain of 2% w/w (batch size: 700 kg). A compression blend was prepared by blending the compressible coated microcapsules and Ceolus at a ratio of 90/10 and compressed into 20 mEq tablets on a production rotary tablet press using scored tooling. The tablets exhibited poor hardness and friability values.

Examples 10 to 13 in Accordance with Aspects of the Invention

Example 10

Microcapsules of KCl crystals (690 kg) were coated to achieve a weight gain of 2% with an aqueous solution of polyvinylpyrrolidone (13.7 kg) and dibutyl sebacate (0.42 kg) at a ratio of 97/3 in a fluid bed coater. A compression blend (batch size: about 780 kg) comprising 89.87 parts of the compressible coated microcapsules, 9.98 parts of microcrystalline cellulose (Ceolus) and 0.15 part of colloidal silicon dioxide (Cab-O-Sil), was compressed into 20 mEq tablets. The capsule shaped monogrammed tablets (¾"×⅜") weighing about 2 g, exhibited a mean hardness of about 18 kP and a friability of 0.1% and a controlled release profile (FIG. 1) equivalent to the commercially available K-Dur 20.

Figure 2:
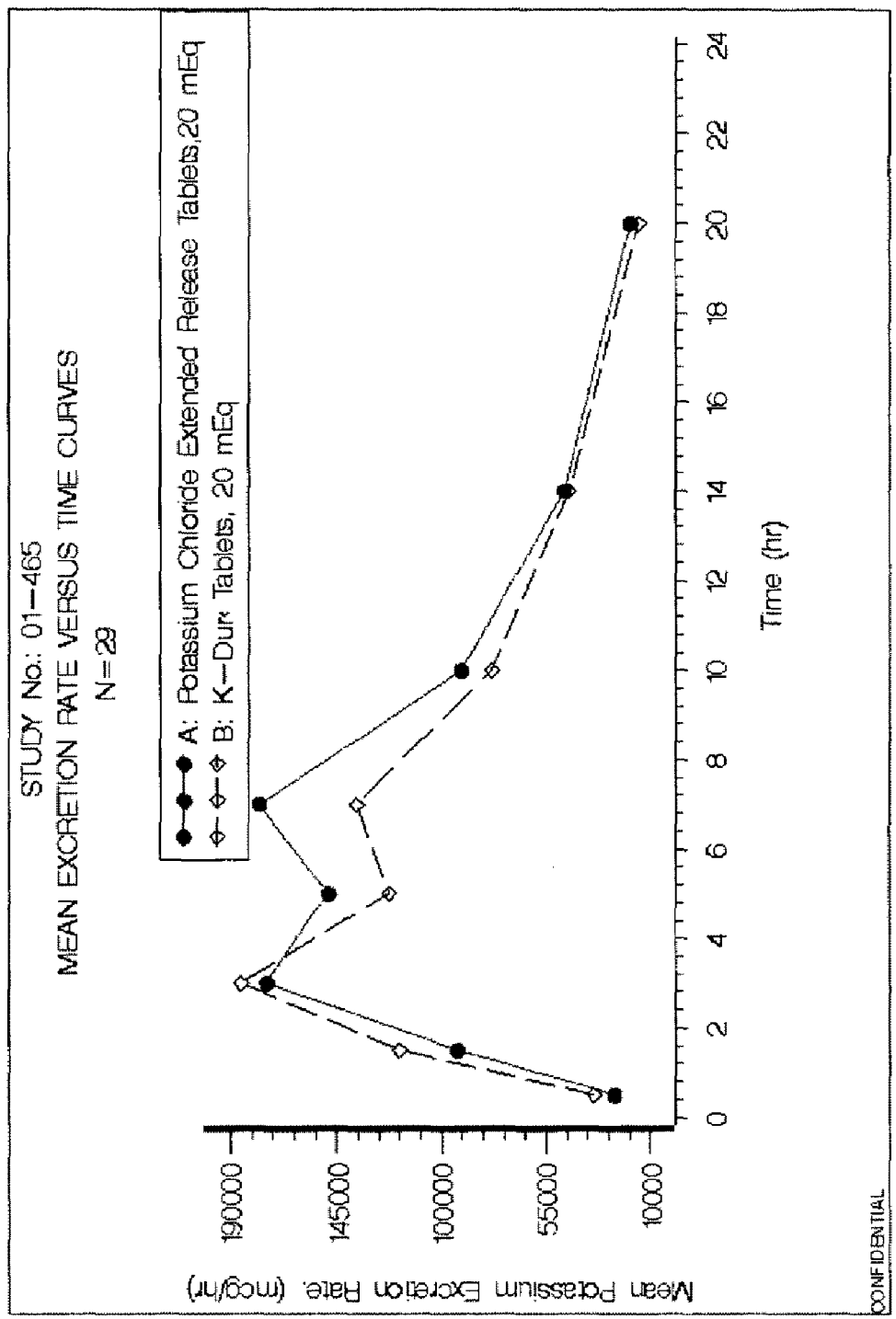
FIG. 2 shows plasma levels of potassium following oral dosing—comparison between 20 mEq controlled release potassium chloride tablets of Example 10, which do not disperse into granules on contact with water or body fluids, versus reference standard (K-Dur) of equal strength.

The results of an open-label, single dose, randomized, two-way crossover bioequivalence study comparing 20 mEq potassium chloride controlled release tablets of Example 10 (marked A in FIG. 2) and reference tablets manufactured and marketed per disclosure of Hsiao and Chou (marked B in FIG. 2) confirmed bioequivalence between the two tablet formulations based on (EAI PF220EA001 versus K-Dur 20 (lot# 1D0110)), in healthy subjects under fasting conditions. Thirty (30) healthy, non-smoking, male subjects aged 20 to 40 years, meeting a set of acceptance and exclusion criteria, were selected, confined to the clinic, and conditioned with standardized meals (maintaining both sodium and potassium intakes) and fixed quantity of water at predetermined intervals during the equilibration periods. Urine samples were collected at the end of equilibrium period (days 5, 6 and days 13, 14) and on dosing days (days 7 and 15) for timed intervals of 0-1, 1-2, 2-4, 4-6, 6-8, 8-12, 12-16, 16-24. The urine samples collected during the BE study were tested for potassium and creatinine concentrations using validated bioanalytical methods.

Even though the tablets of Example 10 were bioequivalent to K-Dur 20, the tablets were not considered to be generically equivalent to K-Dur 20 because the tablets of Example 10 failed to disperse in water within 2 minutes as required for K-Dur® (see Physicians' Desk Reference, page 3047 of PDR Edition 57, 2003).

Example 11

Figure 3:
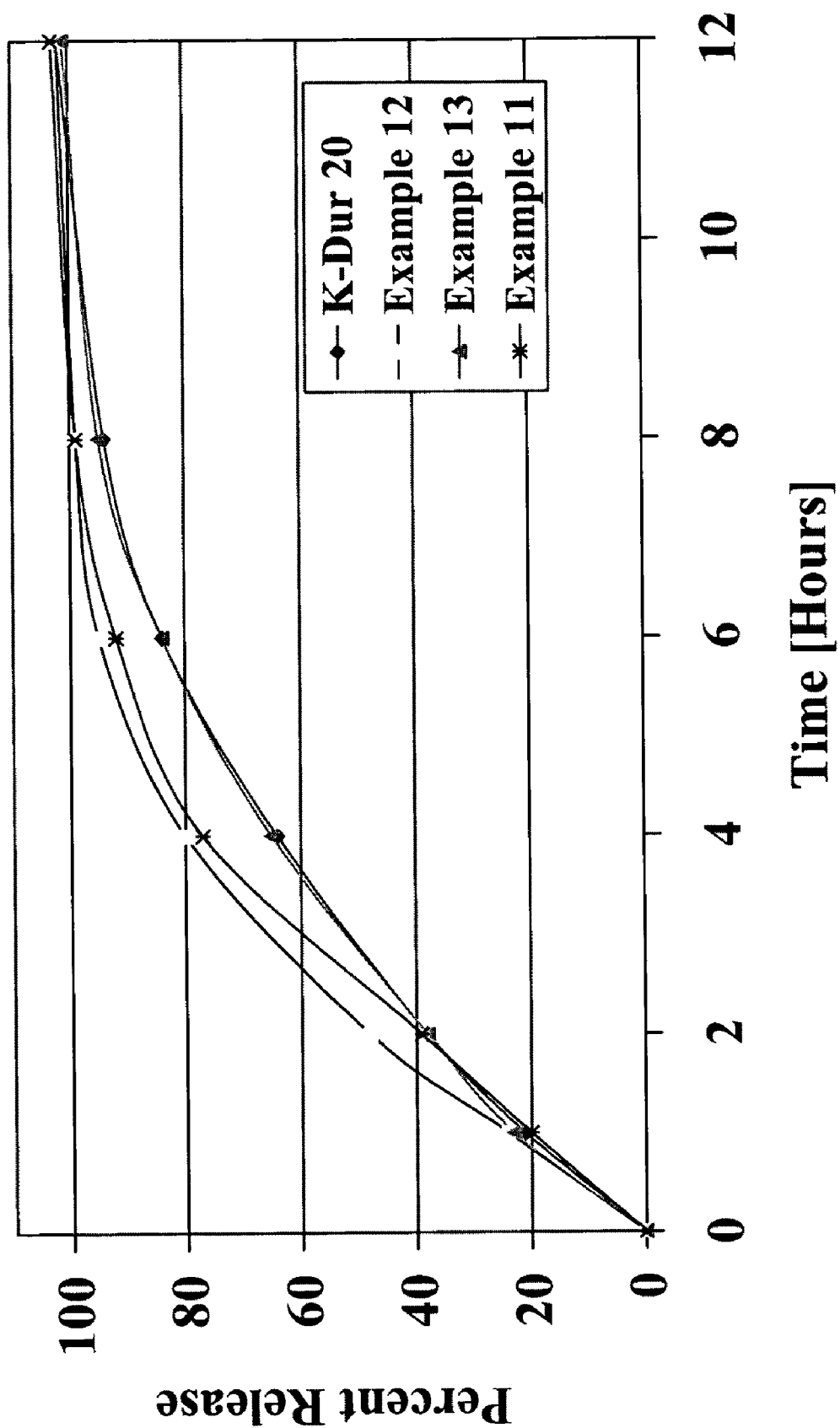
FIG. 3 shows in vitro drug release profiles for 20 mEq controlled release potassium chloride tablets of Examples 11, 12 and 13, which exhibit in vitro or in vivo properties similar to those of reference tablets of equal strength (K-Dur 20 or Hsiao tablets), i.e., not only disperse rapidly into granules on contact with water or body fluids, but also exhibit similar drug release profiles when dissolution tested in 900 mL of purified water at 37° C. using USP Apparatus 2 (paddles@ 50 rpm).

Microcapsules of KCl crystals (batch size: 400 kg) were coated to achieve a weight gain of 2% with an aqueous dispersion of ethylcellulose (commercially available as Aquacoat ECD30 latex dispersion from FMC, Philadelphia, Pa.) and diethyl phthalate at a ratio of 76/24 in a fluid bed coater. A compression blend comprising 85.5 parts of compressible coated Microcaps KCl, 11.9 parts of Ceolus, 2.0 part of Crospovidone, 0.3 part of colloidal silicon dioxide, and 0.3 part of sodium lauryl sulfate were compressed into 20 mEq ER tablets. The capsule shaped monogrammed tablets (¾"× ⅜") weighing about 2 g, exhibited a mean hardness of about 19.1 kP and a friability of 0.17% and rapidly dispersed into granules (microcapsules) on contact with water like the reference tablets, K-Dur 20 manufactured based on the disclosure of Hsiao. Furthermore, these tablets exhibited a controlled release profile similar to that of reference tablets, as shown in FIG. 3.

Example 12

400 kg of Microcaps KCl from production were coated with an aqueous dispersion of ethycellulose, Aquacoat® ECD-30 plasticized with diethyl phthalate (ratio: 60/40) for 4% weight gain. 85.85 parts of compressible coated Microcaps KCl, 12.0 parts of Ceolus, 2.0 part of Crospovidone, and 0.15 part of colloidal silicon dioxide were blended and compressed into 20 mEq ER tablets with a mean hardness of 22.4 kP and a friability of 0.13%. These tablets disintegrated within a minute and exhibited a drug release profile as shown in FIG. 3.

Example 13

Microcaps KCl from production coated with an ethylcellulose dispersion, plasticized with diethyl phthalate (ratio: 76/24) for 2% weight gain. 85.7 parts of compressible coated Microcaps KCl, 12 parts of Ceolus, 2 parts of Crospovidone, and 0.3 part of colloidal silicon dioxide were compressed into 20 mEq ER tablets with a mean hardness of 19.8 kP and a friability of 0.25%. These tablets disintegrated within a minute and exhibited a drug release profile as shown in FIG. 3.

The above examples are provided to show how to practice the present invention and are not intended to be exhaustive or to include all obvious modifications and variations which will become apparent to those skilled in formulation development. However, all these modifications are within the scope of the present invention and by the following claims:

What is claimed is:

1. A process for preparing a controlled release tablet of potassium chloride comprising:
   (a) microencapsulating potassium chloride crystals with an inner membrane comprising ethylcellulose by coacervation or phase separation to form potassium chloride microcapsules;
   (b) coating said potassium chloride microcapsules with an outer membrane comprising a plasticized polymer to form compressible coated microcapsules;
   (c) preparing a compressible blend comprising said compressible coated microcapsules, microcrystalline cellulose, and colloidal silicon dioxide; and
   (d) compressing said compressible blend into tablets,
   wherein the tablet hardness is at least about 14 kP, the friability of the tablets does not exceed about 0.3%, and the tablet exhibits a dissolution profile substantially corresponding to the following pattern when tested by USP Apparatus 2 (Paddles @50 rpm) in purified water:
   after 2 hours, about 30% to about 50% of the total potassium chloride is released;
   after 4 hours, about 60% to about 75% of the total potassium chloride is released; and
   after 8 hours, not less than 80% of the total potassium chloride is released, wherein said plasticized polymer comprises a polymer selected from the group consisting of ethylcellulose, polyvinylpyrrolidone, and hydroxypropyl methylcellulose, wherein said colloidal silicon dioxide is present in an amount of from about 0.1% to about 0.3% by weight of said tablet, wherein said outer membrane coating comprises from about 0.5% to about 5.0% by weight of said compressible coated microcapsules, and wherein said compressible blend is substantially free of lubricants.

2. The process of claim 1, wherein said compressible blend further comprises a disintegrant.

3. The process of claim 2 wherein said disintegrant is present in an amount of from about 0.5% to about 5.0% by weight based on the tablet weight.

4. The process of claim 1 wherein said plasticized polymer comprises ethylcellulose and said coating step comprises coating said potassium chloride microcapsules with an aqueous dispersion of ethylcellulose.

5. The process of claim 4 wherein said plasticized polymer comprises ethylcellulose and diethyl phthalate.

6. The process of claim 1 wherein said microcrystalline cellulose comprises not more than about 15% by weight of said tablet.

7. The process of claim 1 wherein the inner membrane comprises ethylcellulose having a viscosity between about 90 cps and about 110 cps.

8. The process of claim 7 wherein said ethylcellulose forming the inner membrane comprises between about 8% and about 20% by weight of said potassium chloride microcapsules.

9. The process of claim 3 wherein said compressible blend further comprises from about 0.1% to about 1.0% of a surfactant based on the weight of said tablet.

10. The process of claim 1 wherein said plasticized polymer comprises a plasticizer selected from the group consisting of dibutyl sebacate, diethyl phthalate, triacetin, triethyl citrate, polyethylene glycols of different molecular weights and mixtures thereof.

11. The process of claim 10 wherein said plasticizer comprises from about 2% to 40% based on the weight of the plasticized polymer.

12. The process of claim 1 wherein said plasticized polymer comprises hydroxypropyl methylcellulose and polyethylene glycol 400.

13. The process of claim 1 wherein said plasticized polymer comprises ethylcellulose and diethyl phthalate, and wherein said compressible blend comprises about 0.1% to 0.2% by weight colloidal silicon dioxide and not more than about 15% by weight of said microcrystalline cellulose.

14. The process of claim 13, said compressible blend further comprising a disintegrant present in an amount of from about 0.5% to about 3% by weight of said compressible blend.

15. A controlled release potassium chloride tablet prepared by the process of claim 1.

16. A controlled release potassium chloride tablet comprising
   a) a plurality of microcapsules wherein said microcapsules comprise a potassium chloride crystal, an inner membrane on said crystal comprising ethyl cellulose, and an outer membrane surrounding said inner membrane comprising a plasticized polymer;
   b) colloidal silicone dioxide; and
   c) microcrystalline cellulose,
   wherein the tablet hardness is at least about 14 kP, the friability of the tablets does not exceed about 0.3%, and the tablets exhibits a dissolution profile substantially corresponding to the following pattern when tested by USP Apparatus 2 (Paddles @50 rpm) in purified water:
   after 2 hours, about 30% to about 50% of the total potassium chloride is released;
   after 4 hours, about 60% to about 75% of the total potassium chloride is released; and
   after 8 hours, not less than 80% of the total potassium chloride is released, wherein said plasticized polymer comprises a polymer selected from the group consisting of ethylcellulose, polyvinylpyrrolidone, and hydroxypropyl methylcellulose, wherein said colloidal silicon dioxide is present in an amount of from about 0.1% to about 0.3% by weight of said tablet, wherein said outer membrane coating comprises from about 0.5% to about 5.0% by weight of said compressible coated microcapsules, and wherein said tablet is substantially free of lubricants.

17. The controlled release potassium chloride tablet of claim 16 wherein said inner membrane comprises between about 8% and about 20% by weight of said microcapsules.

18. The controlled release potassium chloride tablet of claim 16 wherein said tablet further comprises a disintegrant.

19. The controlled release potassium chloride tablet of claim 18 wherein said disintegrant is selected from the group consisting of sodium starch glycolate, croscarmellose sodium, and cross-linked polyvinylpyrrolidone.

20. The controlled release potassium chloride tablet of claim 16 wherein the potassium chloride is present in an amount effective for the treatment of potassium deficiency in humans by oral administration.

21. The controlled release potassium chloride tablet of claim 16 wherein said plasticized polymer comprises ethyl cellulose and diethyl phthalate.

22. A method of treating potassium deficiency in a subject in need of potassium, comprising administering to the subject an effective amount of the controlled release potassium chloride tablet of claim 16.

23. The controlled release potassium chloride tablet of claim 16, wherein said microcrystalline cellulose is present in an amount of not more than about 15% by weight of the total tablet weight.

24. The process of claim 2, wherein said disintegrant is selected from the group consisting of sodium glycolate, croscarmellose sodium, cross-linked polyvinylpyrrolidone, and combinations thereof.

25. The controlled release potassium chloride tablet of claim 16, further comprising a disintegrant and optionally a surfactant.

26. The controlled release potassium chloride tablet of claim 16, wherein said plasticized polymer comprises a plasticizer selected from the group consisting of dibutyl sebacate, diethyl phthalate, triacetin, triethyl citrate, polyethylene glycols of different molecular weights, and mixtures thereof.

27. The controlled release potassium chloride tablet of claim 16, wherein said plasticized polymer comprises from about 2% to 40% of the plasticizer.

* * * * *

UNITED STATES PATENT AND TRADEMARK OFFICE
CERTIFICATE OF CORRECTION

PATENT NO. : 7,632,521 B2  Page 1 of 1
APPLICATION NO. : 10/619924
DATED : December 15, 2009
INVENTOR(S) : Venkatesh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 776 days.

Signed and Sealed this

Twenty-first Day of December, 2010

David J. Kappos
*Director of the United States Patent and Trademark Office*